United States Patent
Yuan et al.

[11] Patent Number: 5,929,246
[45] Date of Patent: Jul. 27, 1999

[54] N-AMINOALKYLDIBENZOTHIOPHENE CARBOXAMIDES; NEW DOPAMINE RECEPTOR SUBTYPE SPECIFIC LIGANDS

[75] Inventors: Jun Yuan, Clinton; Xi Chen, New Haven, both of Conn.

[73] Assignee: Neurogen Corporation, Branford, Conn.

[21] Appl. No.: 09/088,331

[22] Filed: Jun. 1, 1998

Related U.S. Application Data

[63] Continuation of application No. 08/619,429, Mar. 21, 1996, Pat. No. 5,763,609.

[51] Int. Cl.$^6$ ................ C07D 409/12; C07D 409/14
[52] U.S. Cl. ................ 546/281.1; 546/146; 546/175; 546/194; 546/202; 546/256; 544/333
[58] Field of Search ................ 546/281.1, 256, 546/146, 175, 194, 202; 544/333

[56] References Cited

U.S. PATENT DOCUMENTS

| | | | |
|---|---|---|---|
| 3,952,014 | 4/1976 | Albrecht et al. | 546/202 |
| 4,146,624 | 3/1979 | Albrecht et al. | 544/375 |
| 5,395,835 | 3/1995 | Glase et al. | 514/254 |
| 5,659,033 | 8/1997 | Yuan et al. | 544/380 |
| 5,703,235 | 12/1997 | Yuan et al. | 544/363 |
| 5,763,609 | 6/1998 | Yuan et al. | 544/363 |

OTHER PUBLICATIONS

Protiva et al., *Chemical Abstracts*, vol. 73, No. 98941 (1970).
Pelz et al., *Chemical Abstracts*, vol. 69, No. 86737 (1968).

Primary Examiner—Emily Bernhardt
Attorney, Agent, or Firm—McDonnell, Boehnen, Hulbert & Berghoff

[57] ABSTRACT

Disclosed are compounds of the formula:

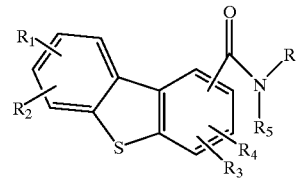

or the pharmaceutically acceptable acid addition salts thereof, wherein:

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —CONR'R", or —NR'R" where R' and R" independently represent hydrogen or $C_1$–$C_6$ alkyl;

R5 is hydrogen or $C_1$–$C_6$ alkyl; and

R represents an aminoalkyl group, which compounds are useful in the treatment of affective disorders such as schizophrenia, depression, Alzheimer's disease, movement disorders such as Parkinsonism and dystonia, and other disorders which respond to dopaminergic blockade such as substance abuse and obsessive compulsive disorders. Further, compounds of this invention may be useful in treating the extrapyramidal side effects associated with the use of conventional neuroleptic agents.

7 Claims, No Drawings

N-AMINOALKYLDIBENZOTHIOPHENE CARBOXAMIDES; NEW DOPAMINE RECEPTOR SUBTYPE SPECIFIC LIGANDS

This is a continuation of application Ser. No. 08/619,429, filed Mar. 21, 1996 now U.S. Pat. No. 5,763,609.

BACKGROUND OF THE INVENTION

1. Field of the Invention

This invention relates to dibenzothiophenecarboxamide derivatives which selectively bind to brain dopamine receptor subtypes. More specifically, it relates to N-aminoalkyldibenzothiophenecarboxamides and to pharmaceutical compositions comprising such compounds. It further relates to the use of such compounds in the treatment or prevention of various neuropsychochological disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_3$ receptor subtype has recently been identified (Sokoloff et al., Nature, 347: 146 (1990). Its unique localization in limbic brain areas and its differential recognition of various antipsychotics suggest that the $D_3$ receptor may play a major role in the etiology of schizophrenia Selective $D_3$ antagonists may be effective antipsychotics free from the neurological side effects displayed by conventional neuroleptics. Compounds of the present invention demonstrate high affinity and selectivity in binding to the $D_3$ receptor subtype. They may be of potential use in treatment of schizophrenia, psychotic depression and mania. Other dopamine-mediated diseases such as Parkinsonism and tardive dyskinesias may also be treated directly or indirectly by modulation of $D_3$ receptors.

U.S. Pat. No. 5,395,835 discloses N-aminoalkyl-2-napthalamides which have affinity at doparnine $D_3$ receptors. The compounds the present invention differ significantly from this prior art in that they possess a dibenzothiophenecarboxamide substructure.

Murray et al., in Bioorg. Med. Chem. Let., 5: 219 (1995), describes 4-carboxamido-biphenyls said to have affinity for dopamine $D_3$ receptors.

SUMMARY OF THE INVENTION

This invention provides novel compounds of Formula I which interact with dopamine receptor subtypes. Thus, the invention provides compounds of general Formula I useful in the treatment and/or prevention of various neuropsychological disorders. The invention also provides pharmaceutical compositions comprising compounds of Formula 1.

The invention further relates to the use of such compounds and compositions in the treatment of affective disorders such as schizophrenia, depression, Alzheimer's disease and certain movement disorders such as Parkinsonism and dystonia. Compounds of this invention are also useful in treating the extrapyramidal side effects associated with the use of conventional neuroleptic agents. Further, the compounds of the present invention are useful for the treatment of other disorders which respond to dopaminergic blockade such as substance abuse and obsessive compulsive disorder.

Since dopamine $D_3$ receptors are concentrated in the limbic system (Taubes, Science 265 (1994) 1034) which controls cognition and emotion, compounds which interact with these receptors also have utility in the treatment of cognitive disorders. Such disorders include cognitive deficits which are a significant component of the negative symptoms (social withdrawal and unresponsiveness) of schizophrenia. Other disorders involving memory impairment or attention deficit disorders can also be treated with the compounds of this invention that interact specifically with the dopamine $D_3$ receptor subtype.

Furthermore, compounds of this invention may be useful in treatment of depression, memory-impairment or Alzheimer's disease by modulation of $D_3$ receptors which selectively exist in limbic area known to control emotion and cognitive functions. The compounds of the present invention are also useful for the treatment of other disorders which respond to dopaminergic blockade such as substance abuse (Caine and Koob, Science, 260: 1814 (1993)) and obsessive compulsive disorder (Goodman et al., Clin. Psychopharmacol., 7: 35 (1992)). The interaction of the compounds of the invention with dopamine receptor subtypes is demonstrated below. This interaction results in the pharmacological activities of these compounds.

Accordingly, a broad embodiment of the invention is directed to a compound of Formula 1:

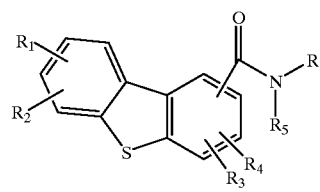

or the pharmaceutically acceptable acid addition salts thereof, wherein:

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —CONR'R", or —NR'R" where R' and R" independently represent hydrogen or $C_1$–$C_6$ alkyl;

$R_5$ is hydrogen or $C_1$–$C_6$ alkyl; and

R represents an aminoalkyl group.

Thus, the invention relates to the use of compounds of formula I in the treatment and/or prevention of neuropsychochological disorders including, but not limited to, schizophrenia, mania, dementia, depression, anxiety, compulsive behavior, substance abuse, memory impairment, cognitive deficits, Parkinson-like motor disorders and motion disorders related to the use of neuroleptic agents.

DETAILED DESCRIPTION OF THE INVENTION

In addition to compounds of general formula I described above, the invention encompasses compounds of general formula IA:

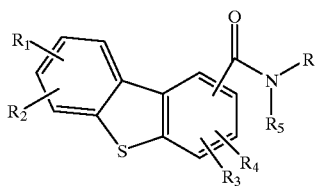

wherein:

R₁, R₂, R₃, R₄, R₅ are as defined above; and
R represents an aminoalkyl group of the formula

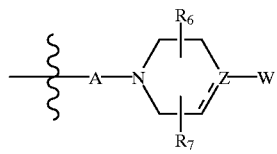

where

A represents an alkylene group of 2 to 6 carbon atoms optionally substituted with one or more alkyl groups having from 1 to 4 carbon atoms;

Z is N or C;

$R_6$ and $R_7$ are the same or different and represent hydrogen or $C_1$–$C_6$ alkyl; or $R_6$ and $R_7$ together with the the 6-membered ring to which they are attached form a 5 to 8-membered ring; and W is phenyl, naphthyl, 1-(5,6,7,8-tetrahydro)naphthyl or 4-(1,2-dihydro)indenyl, pyridinyl, pyrimidyl, quinolinyl, isoquinolinyl, benzofuranyl, benzothienyl; each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoronethyl or trifluoromethoxy.

Preferred compounds of formula IA include those where $R_1$–$R_4$ are hydrogen and A is alkylene of 3–5 carbon atoms.

In addition to compounds of general formula I described above, the invention encompasses compounds of general formula IB:

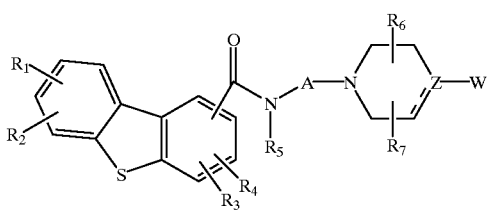

wherein:

$R_1$, $R_2$, $R_3$, $R_4$, and $R_5$ are as defined above;

$R_6$ and $R_7$ are the same or different and represent hydrogen or $C_1$–$C_6$ alkyl; or $R_6$ and $R_7$ together with the the 6membered ring to which they are attached form a 5 to 8-membered ring; and A, Z and W are as defined above.

The present invention further encompasses compounds of Formula II:

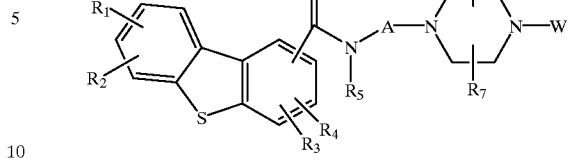

wherein $R_1$, $R_2$, $R_3$, $R_4$, $R_5$, $R_6$, and $R_7$, A, and W are as defined above.

Preferred compounds of formula II are those where $R_1$–$R_5$ are hydrogen; A is $C_3$–$C_5$ alkylene; and W is quinolinyl, naphthyl or a phenyl group optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy. More preferred compounds of formula II are those where $R_1$–$R_5$ are hydrogen; A is $C_3$–$C_5$ alkylene; and W is 8quinolinyl, naphthyl or a phenyl group optionally substituted with up to two groups in the 2 and/or 3 positions (relative to the point of attachment of the phenyl group to the piperazine ring), the groups being independently selected from halogen, $C_1$–$C_4$ alkyl, and $C_1$–$C_4$ alkoxy. Particularly preferred compounds of formula II are those where $R_1$–$R_5$ are hydrogen; A is $C_4$ alkylene; and W is 8-quinolinyl, naphthyl or a phenyl group optionally up to two groups in the 2 and/or 3 positions (relative to the point of attachment of the phenyl group to the piperazine ring), the groups being independently selected from chloro, methyl, and methoxy.

The present invention further encompasses compounds of Formula III:

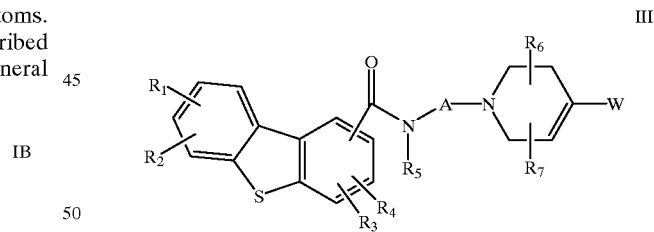

wherein $R_1$, $R_2$, $R_3$, $R_4$, $R_5$, $R_6$, and $R_7$, A, and W are as defined above.

Preferred compounds of formula III are those where $R_1$–$R_5$ are hydrogen; A is $C_3$–$C_5$ alkylene, more preferably butylene; and W is quinolinyl, naphthyl or phenyl optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy. Particularly preferred compounds of formula III are those where $R_1$–$R_5$ are hydrogen; A is $C_3$–$C_5$ alkylene, more preferably butylene; and W is 8-quinolinyl, naphthyl, or phenyl.

The invention also provides compounds of Formula IV

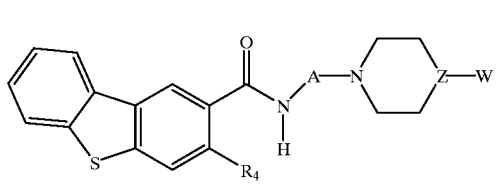

IV where
  $R_4$ is hydrogen or $C_1$–$C_4$ alkoxy;
  A represents alkylene group of 2 to 6 carbon atoms;
  Z is nitrogen or carbon; and
  W is quinolinyl, phenyl or naphthyl, each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

Preferred compounds of formula IV are those where $R_4$ is hydrogen and A is $C_3$–$C_5$ alkylene. More preferred compounds of formula IV are those where $R_4$ is hydrogen; A is $C_4$ alkylene; Z is nitrogen; and W is 8-quinolinyl, naphthyl or phenyl optionally substituted with up to two groups in the 2 and/or 3 positions (relative to the point of attachment of the phenyl group to the 6-membered nitrogen-containing ring), the groups being independently selected from halogen, $C_1$–$C_4$ alkyl, and $C_1$–$C_4$ alkoxy.

The invention further provides compounds of Formula V

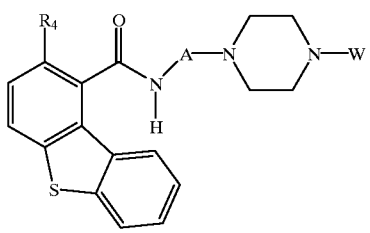

V where
  $R_4$ is hydrogen or $C_1$–$C_4$ alkoxy;
  A represents alkylene group of 2 to 6 carbon atoms; and
  W is quinolinyl, phenyl or naphthyl, each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

Preferred compounds of formula V are those where $R_4$ is $C_1$–$C_4$ alkoxy and A is $C_3$–$C_5$ alkylene. More preferred compounds of formula V are those where $R_4$ is $C_1$–$C_4$ alkoxy; A is $C_4$ alkylene; and W is 8-quinolinyl, naphthyl or phenyl optionally substituted with up to two groups in the 2 and/or 3 positions (relative to the point of attachment of the phenyl group to the piperazine ring), the groups being independently selected from halogen, $C_1$–$C_4$ alkyl, and $C_1$–$C_4$ alkoxy. Particularly preferred compounds of formula V are those where $R_4$ is $C_1$–$C_4$ alkoxy; A is $C_4$ alkylene; and W is 8-quinolinyl, naphthyl, or a phenyl group substituted in the 2 position (relative to the point of attachment of the phenyl group to the piperazine ring) with a $C_1$–$C_4$ alkoxy, preferably methoxy, group.

The invention also provides compounds of Formula VI

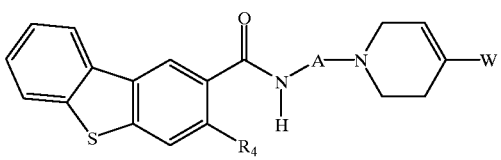

VI where
  $R_4$ is hydrogen or $C_1$–$C_4$ alkoxy;
  A represents alkylene group of 2 to 6 carbon atoms; and
  W is quinolinyl, phenyl or naphthyl, each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

Preferred compounds of formula VI are those where $R_4$ is hydrogen and A is $C_3$–$C_5$ alkylene. More preferred compounds of formula VI are those where $R_4$ is hydrogen; A is $C_4$ alkylene; and W is 8-quinolinyl, naphthyl or phenyl optionally substituted with up to two groups in the 2 and/or 3 positions (relative to the point of attachment of the phenyl group to the 6-membered nitrogen-containing ring), the groups being independently selected from halogen, $C_1$–$C_4$ alkyl, and $C_1$–$C_4$ alkoxy.

The invention also provides compounds of Formula VI-A

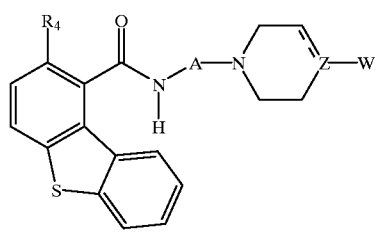

VI-A where
  $R_4$ is hydrogen or $C_1$–$C_4$ alkoxy;
  A represents alkylene group of 2 to 6 carbon atoms;
  Z is nitrogen or carbon; and
  W is quinolinyl, phenyl or naphthyl, each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

Preferred compounds of formula VI-A are those where $R_4$ is hydrogen and A is $C_3$–$C_5$ alkylene. More preferred compounds of formula VI-A are those where $R_4$ is hydrogen; A is $C_4$ alkylene; Z is nitrogen; and W is 8-quinolinyl, naphthyl or phenyl optionally substituted with up to two groups in the 2 and/or 3 positions (relative to the point of attachment of the phenyl group to the 6-membered nitrogen-containing ring), the groups being independently selected from halogen, $C_1$–$C_4$ alkyl, and $C_1$–$C_4$ alkoxy.

When a compound of the invention is obtained as a mixture of enantiomers, these enantiomers may be separated, when desired, by conventional methods such as crystallization in the presence of a resolving agent, or chromatography, for example using a chiral HPLC column.

Representative compounds of the present invention, which are encompassed by Formula I, include, but are not limited to the compounds in FIG. I and their pharmaceutically acceptable salts. The present invention also encompasses prodrugs, e.g., acylated prodrugs, of the compounds of Formula I. Those skilled in the art will recognize various synthetic methodologies which may be employed to prepare non-toxic pharmaceutically acceptable addition salts and prodrugs of the compounds encompassed by Formula I.

Representative compounds of the present invention, which are encompassed by Formula I, include, but are not limited to the compounds in Table 1 and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0–4, and the like. Those skilled in the art will recognize a wide variety of non-toxic pharmaceutically acceptable addition salts.

The following numbering system is used to identify positions on the dibenzofuran ring portion of the compounds of the invention:

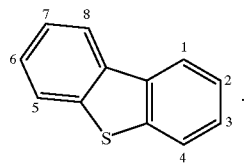

By "alky" and "lower alkyl" is meant straight and branched chain alkyl groups having from 1–6 carbon atoms, e.g., $C_1-C_6$ alkyl.

By "lower alkoxy" and "alkoxy" is meant straight and branched chain alkoxy groups having from 1–6 carbon atoms, e.g., $C_1-C_6$ alkoxy.

By halogen is meant fluorine, chlorine, bromine and iodine.

The amino portion of the aminoalkyl group represented by R above includes groups represented by the formula Q

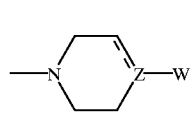

where W is defined above.

Th formula Q represents saturated heterocyclic ring systems such as, for example, piperidinyl and piperazinyl, as well as unsaturated heterocyclic ring systems such as, for example, 1, 2, 3, 6-tetrahydropyrindine. Preferred Q groups are the following:

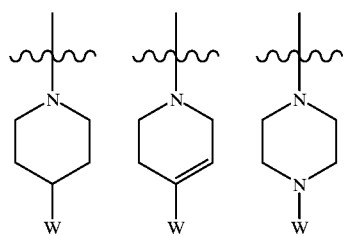

where W is defined above.

Particularly preferred W groups of the invention are (a) quinolinyl, more preferably 8-quinolinyl, (b) naphthyl, or (c) phenyl optionally substituted with up to two substituents independently selected from halogen, $C_1-C_4$ alkyl, and $C_1-C_4$ alkoxy. These optional phenyl substituents are preferably in the 2 and/or 3 positions of the phenyl group relative to the point of attachment of the phenyl group to the 6-membered nitrogen containing ring.

Representative examples of N-aminoalkyldibenzothiophenecarboxamides according to the invention are shown in Table 1 below. The number below each compound is its compound number. Each of these compounds may be prepared according to the general reaction Scheme I set forth below.

Compounds 1–8 in Table 1 have the following general formula A:

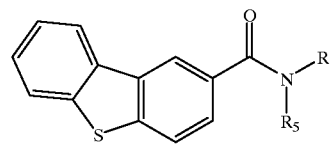

where R and $R_5$ are defined in the table.

Compounds 9–11 in Table 1 have the following general formula B:

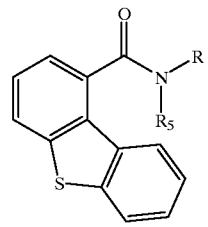

where R and $R_5$ are defined in the table.

TABLE 1

| Compound Number | $R_5$ | R |
|---|---|---|
| 1 | H | ![structure with piperazine-dichlorophenyl] |
| 2 | H | ![structure with piperazine-naphthyl] |
| 3 | H | ![structure with piperazine-methyl-chlorophenyl] |

TABLE 1-continued

| Compound Number | $R_5$ | R |
|---|---|---|
| 4 | H | butyl-piperazinyl-(2,3-dimethylphenyl) |
| 5 | H | butyl-piperazinyl-(2-chlorophenyl) |
| 6 | H | butyl-piperazinyl-(2-methylphenyl) |
| 7 | H | butyl-piperazinyl-(8-quinolinyl) |
| 8 | H | butyl-(4-phenyl-1,2,3,6-tetrahydropyridin-1-yl) |
| 9 | H | butyl-piperazinyl-(2,3-dichlorophenyl) |
| 10 | H | butyl-piperazinyl-(1-naphthyl) |
| 11 | H | ethyl-piperazinyl-(1-naphthyl) |

Particular compounds according to the invention include:

N-(1-{4-[4-(2,3-Dichlorophenyl)piperazin-1-yl]}butyl)-2-dibenzothiophenecarboxamide hydrochloride N-(1-{4-[4-(1-Naphthyl)piperazin-1-yl]}butyl)-2-dibenzothiophenecarboxamide hydrochloride N-(1-{4-[4-(2-Methyl-3chlorophenyl)piperazin-1-yl]}butyl)-2-dibenzothiophenecarboxamide hydrochloride N-(1-{4-[4-(2,3-Dimethylphenyl)piperazin-1-yl]}butyl)-2-dibenzothiophenecarboxamide hydrochloride N-(1-{4-[4-(2-Chlorophenyl)piperazin-1-yl]}butyl)-2dibenzothiophenecarboxamide hydrochloride N-(1-{4-[4-(2-Methylphenyl)piperazin-1-yl]}butyl)-2-dibenzothiophenecarboxamide hydrochloride N-(1-{4-[4-(8-Quinolinyl)piperazin-1-yl]}butyl)-2dibenzothiophenecarboxamide hydrochloride N-(1-{4-[4-Phenyl-1,2,3,6tetrahydropyridin-1-y1]}butyl)-2-dibenzothiophenecarboxamide hydrochloride N-(1-{4-[4-(2,3-Dichlorophenyl)piperazin-1-yl]}butyl)-1-dibenzothiophenecarboxamide hydrochloride N-(1-{4-[4-(1-Naphthyl)piperazin-1-yl]}butyl)-1-dibenzothiophenecarboxamide hydrochloride N-(1-{2-[4-(1-Naphthyl)piperazin-1-yl]}ethyl)-1-dibenzothiophenecarboxamide hydrochloride The invention also pertains to the use of compounds of general Formula I in the treatment of neuropsychological disorders. The pharmaceutical utility of compounds of this invention are indicated by the following assays for dopamine receptor subtype affinity.

ASSAY FOR $D_2$ AND $D_3$ RECEPTOR BINDING ACTIVITY

Pellets of COS cells containing recombinantly produced $D_2$ or $D_3$ receptors from African Green monkey were used for the assays. The sample is homogenized in 100 volumes (w/vol) of 0.05 M Tris HCl buffer at 40° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 mM spiperone; without further additions, nonspecific binding is less than 20% of total binding. The binding characteristics of representative compounds of the invention for $D_2$ and $D_3$ receptor subtypes are shown in Table 2 for rat striatal homogenates.

TABLE 2

| Compound Number[1] | $D_3$ $K_i$ (nM) | $D_2$ $K_i$ (nM) |
|---|---|---|
| 1 | 3.5 | 285 |
| 2 | 5.0 | 242 |

[1]Compound numbers relate to compounds shown above in Table 1.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the and partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preparation of N-aminoalkyldibenzothiophenecarboxamides

The compounds of Formula I, and the pharmaceutically acceptable acid addition salts thereof, may be prepared according to the reactions shown below in Scheme 1.

Scheme 1

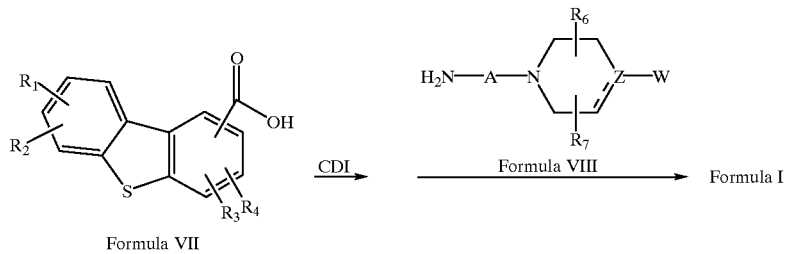

Formula VII wherein $R_1$, $R_2$, $R_3$, $R_4$, $R_5$, $R_6$, $R_7$, A, Z and W are as defined above for Formula IA.

As shown, a compound of Formula VII may be activated by 1,1'-carbonyldiimidazole (CDI) or the like in solvents such as tetrahydrofuran at room temperature. The resulting activated species may be subsequently reacted with the required compound of Formula VIII to afford a compound of Formula I as the desired product.

Where they are not commercially available, the compounds of Formula VII may be prepared by literture procedures or procedures analogous to those described in literature. The compounds of Formula VIII are either known or capable of being prepared by various methods known in the art.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The disclosures in this application of all articles and references, including patents, are incorporated herein by reference.

The invention is illustrated further by the following examples which are not to be construed as limiting the invention in scope or spirit to the specific procedures described in them. These examples illustrate the presently preferred methods for preparing the compounds of the invention.

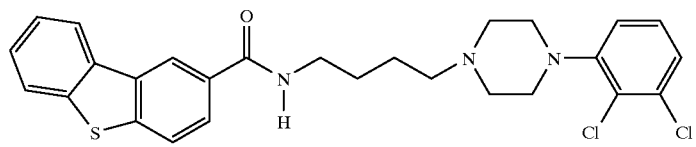

N-(1-{4-[4-(2, 3-Dichlorophenyl)piperazin-1-yl]}-butyl)-2-dibenzothiophenecarboxamide 2-Dibenzothiophenecarboxylic acid (105 mg, 0.45 mmol) and 1,1'-carbonyldiimidazole (80 mg, 0.5 mmol) are stirred in 20 mL tetrahydrofuran at room temperature overnight. A solution of 4-[4-(2,3-dichlorophenyl)piperazin-1-yl]-1-aminobutane (150 mg, 0.5 mmol) in 5 mL of tetrahydrofuran is added. The resulting mixture is stirred for another 2 hours. The reaction mixture is then partitioned between dichloromethane and 10% aqueous sodium bicarbonate solution. The organic layer is dried ($Na_2SO_4$) and concentrated in vacuo. The resulting oil is subjected to preparative TLC using 10:1:0.1 dichloromethane-methanol-ammonium hydroxide as eluent. This affords the title compound as the free base. The hydrochloride salt is prepared by treating the free base with diethyl ether-HCl. The resulting hydrochloride salt of the title compound has a melting point of 238–240° C.

EXAMPLE 2

The following compounds of Formula 1 are prepared essentially according to the procedures set forth in Example 1 above.

(a) N-(1-{4-[4-(1-Naphthyl)piperazin-1-yl]}butyl)-2-dibenzothiophenecarboxamide hydrochloride (mp 225–228° C.)

(b) N-(1-{4-[4-(2-Methyl-3-chlorophenyl)piperazin-1-yl]}butyl)-2-dibenzothiophenecarboxamide hydrochloride (mp 230–231° C.)

(c) N-(1-{4-[4-(2,3-Dimethylphenyl)piperazin-1-yl]}butyl)-2-dibenzothiophenecarboxamide hydrochloride (mp 226–228° C.)

(d) N-(1-{4-[4-(2-Chlorophenyl)piperazin-1-yl]}butyl)-2-dibenzothiophenecarboxamide hydrochloride (mp 226–228° C.)

(e) N-(1-{4-[4-(2-Methylphenyl)piperazin-1-yl]}butyl)-2dibenzothiophenecarboxamide hydrochloride (mp 232–235° C.)

(f) N-(1-{4-[4-(8-Quinolinyl)piperazin-1-yl]}butyl)-2-dibenzothiophenecarboxamide hydrochloride (mp 235–238° C.)

(g) N-(1-{4-[4-Phenyl-1,2,3,tetrahydropyridin-1-yl]}butyl)-2-dibenzothiophenecarboxamide hydrochloride (mp 266–268° C.)

(h) N-(1-{4-[4-(2,3-Dichlorophenyl)piperazin-1-yl]}butyl)-1-dibenzothiophenecarboxamide hydrochloride (mp 220–222° C.)

(i) N-(1-{4-[4-(1-Naphthyl)piperazin-1-yl]}butyl)-1-dibenzothiophenecarboxamide hydrochloride (mp 222–223° C.)

(j) N-(1-{2-[4-(1-Naphthyl)piperazin-1-yl]}ethyl)-1-dibenzothiophenecarboxamide hydrochloride (mp 215–218° C.)

What is claimed is:

1. A compound of the formula:

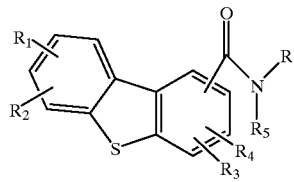

or pharmaceutically acceptable salts thereof wherein:

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR—, —COR', —$SO_mR'$, where R' is $C_1$–$C_6$ alkyl and wherein m is 0, 1 or 2; or $R_1$, $R_2$, $R_3$, $R_4$ independently represent —CONR'R", or —NR'R" where R' and R" independently are hydrogen or $C_1$–$C_6$ alkyl;

$R_5$ is hydrogen or $C_1$–$C_6$ alkyl; and

R represents an aminoalkyl group of the formula

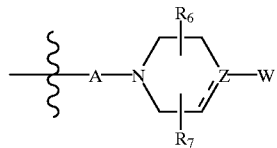

where

A represents an alkylene group of 2 to 6 carbon atoms optionally substituted with one or more alkyl groups having from 1 to 4 carbon atoms;

Z is C or CH;

$R_6$ and $R_7$ are the same or different and represent hydrogen or $C_1$–$C_6$ alkyl; and W is phenyl, naphthyl, 1-(5,6,7,8-tetrahydro)naphthyl or 4-(1,2-dihydro)indenyl, pyridinyl, pyrimidyl, quinolinyl, isoquinolinyl, benzofuranyl, benzothienyl; each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

2. A compound of the formula:

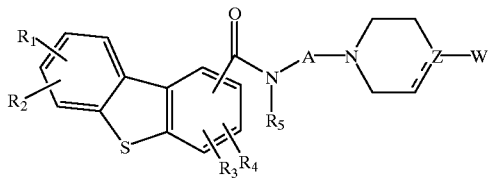

or pharmaceutically acceptable salts thereof wherein:

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR—, —COR', —$SO_mR'$, where R' is $C_1$–$C_6$ alkyl and wherein m is 0, 1 or 2; or $R_1$, $R_2$, $R_3$, $R_4$ independently represent —CONR'R", or —NR'R" where R' and R" independently are hydrogen or $C_1$–$C_6$ alkyl;

$R_5$ is hydrogen or $C_1$–$C_6$ alkyl;

A represents an alkylene group of 3 to 5 carbon atoms;

Z is C or CH; and

W is phenyl, naphthyl, 1-(5,6,7,8-tetrahydro)naphthyl or 4-(1,2-dihydro)indenyl, pyridinyl, pyrimidyl, isoquinolinyl, quinolinyl, benzofuranyl, benzothienyl; each of which is optionally independently substituted with up to three groups selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

3. A compound according to claim 1 which is

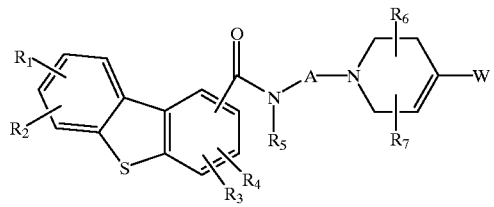

wherein $R_6$ and $R_7$ are the same or different and represent hydrogen or $C_1$–$C_6$ alkyl; and A represents an alkylene group of 2 to 6 carbon atoms optionally substituted with one or more alkyl groups having from 1 to 4 carbon atoms; and W is phenyl, naphthyl, 1-(5,6,7,8-tetrahydro)naphthyl or 4-(1,2-dihydro)indenyl, pyridinyl, pyrimidyl, isoquinolinyl, quinolinyl, benzofuranyl, benzothienyl; each of which is optionally independently substituted with up to three groups selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

4. A compound according to claim 3, wherein $R_1$–$R_5$ are hydrogen; A is $C_3$–$C_5$ alkylene; and W is quinolinyl, naphthyl or phenyl, each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

5. A compound according to claim 3, wherein $R_1$–$R_5$ are hydrogen; A is butylene; and W is 8-quinolinyl, naphthyl, or phenyl.

6. A compound according to claim 1, which is N-(1-{4-[4-Phenyl-1,2,3,6-tetrahydropyridin-1-yl]}butyl)-2-dibenzothiophenecarboxamide hydrochloride.

7. A compound according to claim 1, which is N-(1-{4-[4-Phenyl-1,2,3,6-tetrahydropyridin-1-yl]}butyl)-2-dibenzothiophenecarboxamide.

\* \* \* \* \*